(12) United States Patent
Sanders Acedo

(10) Patent No.: US 10,702,470 B2
(45) Date of Patent: Jul. 7, 2020

(54) CERVICOUTERINE DEVICE THAT INCREASES PROTECTION AGAINST THE RISK OF CONTRACTING CERVICOUTERINE CANCER

(71) Applicant: Guillermo Sanders Acedo, Mexico City (MX)

(72) Inventor: Guillermo Sanders Acedo, Mexico City (MX)

( * ) Notice: Subject to any disclaimer, the term of this patent is extended or adjusted under 35 U.S.C. 154(b) by 1072 days.

(21) Appl. No.: 15/100,900

(22) PCT Filed: Aug. 27, 2015

(86) PCT No.: PCT/MX2015/000121
§ 371 (c)(1),
(2) Date: Jun. 1, 2016

(87) PCT Pub. No.: WO2016/022016
PCT Pub. Date: Feb. 11, 2016

(65) Prior Publication Data
US 2016/0296468 A1    Oct. 13, 2016

(30) Foreign Application Priority Data
Aug. 6, 2014 (MX) .................. MX/A/2014/009494

(51) Int. Cl.
| | | |
|---|---|---|
| *A61K 9/00* | (2006.01) |
| *A61K 33/34* | (2006.01) |
| *A61F 6/14* | (2006.01) |
| *A61K 47/02* | (2006.01) |
| *A61K 47/32* | (2006.01) |
| *A61K 47/34* | (2017.01) |

(52) U.S. Cl.
CPC ............ *A61K 9/0039* (2013.01); *A61F 6/144* (2013.01); *A61K 33/34* (2013.01); *A61K 47/02* (2013.01); *A61K 47/32* (2013.01); *A61K 47/34* (2013.01)

(58) Field of Classification Search
CPC .................................................. A61K 9/0039
See application file for complete search history.

(56) References Cited

U.S. PATENT DOCUMENTS

| | | |
|---|---|---|
| 4,005,707 A | 2/1977 | Moulding, Jr. |
| 4,724,832 A | 2/1988 | Strubel et al. |

FOREIGN PATENT DOCUMENTS

WO        2010086681 A1    8/2010

*Primary Examiner* — Kortney L. Klinkel
(74) *Attorney, Agent, or Firm* — Egbert, McDaniel & Swartz, PLLC

(57) ABSTRACT

A uterine cervical device is provided whose antiviral properties of copper have been directed, broadened and extended to reduce the risk of contracting uterine cervical cancer and act as a preventive factor in cervical carcinogenesis. This is achieved by concentrating, increasing and distributing the copper adjacent the female reproductive apparatus, consisting of the lower part of the uterine cavity and the endocervix, an incubation site of the human papillomavirus, the leading cause of uterine cervical cancer. The device as presented increases the ionic capacity of copper by increasing its surface to 418 mm, and spacing out coils of the winding, incorporating a length of the same material, and positioning it directly in the cervix, which is shaped like a coil, Solomon Bar, bracelet or Celtic Knot, having assembled the copper filaments on a plastic frame of sizes that correspond to the proportions of the uterine cavity according to its parity.

10 Claims, 8 Drawing Sheets

CERVICOUTERINE DEVICE THAT INCREASES PROTECTION AGAINST THE RISK OF CONTRACTING CERVICOUTERINE CANCER

BACKGROUND

Uterine cervical cancer is a public health problem worldwide, primarily affecting women in emerging countries, Mexico included.

German scientist Harald zur Hausen, awarded the Nobel Prize for Medicine in 2008, discovered the major role that the human papillomavirus has in the development of cervical cancer.[1]

In this country (Mexico), according to the Newscure study by Dr. Jose de Jesus Curiel, there are two million women infected with human papillomavirus: HPV and 600 000 have a premalignant lesion in the cervix[2]. Moreover, the National Institute of Public Health, in the document entitled: *Cuentas en Salud Reproductiva y Equidad de Género* (Accounts in Reproductive Health and Gender Equality)[3] reported 4, 169 deaths from cervical-uterine cancer, i.e., one every two hours, more than ninety percent in women over 40 years of age. The reason for this rate of incidence is due to the fact that the virus requires many attempts to alter the cells and takes a long time to do so, which explains why infection is most common in the young and cancer is most common at older ages.

However, there is a contradiction whereby, although it is a pathology that is feasibly cured, if detected in early stages and treated in good time, there continues to be so many deaths, despite the existence of a vaccine, which does not provide complete protection and presents side effects that have led to the suspension of its application in several countries on this continent, in Europe and in Asia.

Moreover, there are efficient, reliable, safe alternatives which, based on extensive scientific studies like the one published in the prestigious scientific-medical journal Lancet Oncology in Great Britain in September 2011, comprising 26 epidemiological studies in eight countries, including Mexico, it was found that the presence of intrauterine devices with copper halved the risk of contracting uterine cervical cancer caused by the human papillomavirus and its ongoing protective effect remains significant for 10 years.[4]

In turn, the US Environment Protection Agency (EPA), alarmed by the high mortality caused by nosocomial infections, sponsored a study whereby the bactericidal, fungicidal and antiviral properties of copper were corroborated, since in the space of two hours, it kills 99.9% of these, including Staphylococcus aureus that is resistant to methicillin, an antibiotic being used to combat super-bacteria.[5]

It has also proven effective against Candida A, which causes vaginitis in Mexican women; and many others, such as the H1N1 influenza virus, adenovirus, *E. coli* 0157 Clostridium difficile, etc.[6]

In Mexico, uterine cervical cancer is the leading cause of neoplasms in women over 25 years. This scourge mainly affects women on low incomes, in places with little or no access to health services, located across countless small, scattered and hard-to-reach localities. There are 10 million people living in 170, 000 localities with less than 500 inhabitants who have scarcely any possibility of being reached by the official programs for early detection through the application of the Papanicolaou test, which often detects very advanced cases of uterine cervical cancer.[7]

As with all public health problems, the solution lies in their prevention. In this area, the 380 A copper-T intrauterine device has played an important preventive role, because in its standard presentation it has been able to reduce the risk of cervical cancer by 50%, even though, despite its dimensions, currently only 7% of women of childbearing age use it due to dimensional incompatibility.[8, 9, 10]

The answer is offered by the uterine cervical device that presents technical innovations consisting, inter alia, of increased copper 418 mm ions.

The present invention develops a preventive method to avoid the transformation of the human papillomavirus into cervical cancer, causing its preventive effects in the region of the female reproductive organs, particularly opposite the cavities that make up the endocervix, significantly reducing this scourge, regardless of accessibility to institutions and affordability

PRIOR ART

The present invention relates to intrauterine devices; it is a substantial improvement related to patent MX213004 DISPOSITIVO INTRAUTERINO T DE COBRE CORTO PARA NULIPARAS MUJERES Y/O BREVILINEAS that protects a contraceptive method.

A uterine cervical device is also known, as described in patent CN102369003 (A) INTRA-CERVICAL DEVICE FOR THE LOCAL RELEASE OF DRUGS IN THE LOCAL-REGIONAL TREATMENT OF CERVICAL CANCER, for local delivery of drugs for the treatment of tumors of the cervix.

There is also a "vaccine" that protects against some types of human papillomavirus. The United States Food and Drug Administration (FDA) has approved two presentations of it.

DESCRIPTION

The present invention describes a uterine cervical device that increases protection against the development of uterine cervical cancer caused mainly by the human papillomavirus, leveraging the antiviral properties of copper by increasing, regrouping and redistributing the copper surface, and its concentration to 82% in the most vulnerable region of the female reproductive system. It consists of a frame of inert plastic such as low-density polyethylene, polypropylene, Dacron or Silastic in a T-shape (FIG. 1 (A, B)) into which is incorporated between 15% and 23% radiopaque barium sulfate and titanium oxide as a dye.

A first innovation consists in the increase and concentration of 418 mm$^2$ of copper as well as its redistribution in the manner detailed in FIG. (1)

A second innovation is that the horizontal arm of the frame (A) has a length between 18.0±2 mm and 32.0±2 mm and a diameter of 1.7 mm on which is wound or coiled a 0.25-0.26 mm strand of copper (C) each of 36 mm$^2$ to give a total of 72.0±2 mm$^2$ forming an aerodynamic shape during the insertion process that eliminates the sharp edge caused by the angle of the cylinders of the same material.

A third innovation is that the vertical post or arm (B), which has 26.0±2 mm and 36.0±2 mm at its lower end has 200 mm$^2$ of copper filament in two layers wound or coiled on it, each with 100 mm$^2$ and 123 mm in length each totaling 200 mm$^2$ (D).

A fourth innovation is the 0.30 mm spaced pitch of the coils (E) which allows double the release of copper ions over the usual winding. The distance of the double winding and the accent of the frame, is between 20.0 and 25.0 mm.

A fifth innovation is that the vertical post or arm has, at its final end a sphere made of plastic and/or copper measuring 3.1 mm in diameter (F).

A sixth innovation is that, within the area of the sphere (G) are located the ends of a length of 99.9% pure copper, oxygen-free winding with a length of between 150 and 300 mm and 146-250 mm$^2$, placed on the uterine cervical canal right opposite the folds or cavities of the cervix, where the human papillomaviruses are incubated, with the possibility that both the length and mm$^2$ of the copper surface may vary, without exceeding the measurements of the cervix or the total 418 mm$^2$ of the total copper surface in uterine cervical device (G).

A seventh innovation is that length can have different shapes, such as a Solomon Bar, Celtic Knot, Bracelet (H, I, J).

The eighth innovation consists of various measurements of the frame that are contained in FIG. (1) in order to achieve the proper operation and tolerance of the uterine cervical device inside the uterine cavity.

The ninth innovation, consists of a plunger or piston which has a recess at its final end to lodge the extension of the uterine cervical device into the cervical canal. (FIG. 8)

Figure 1:
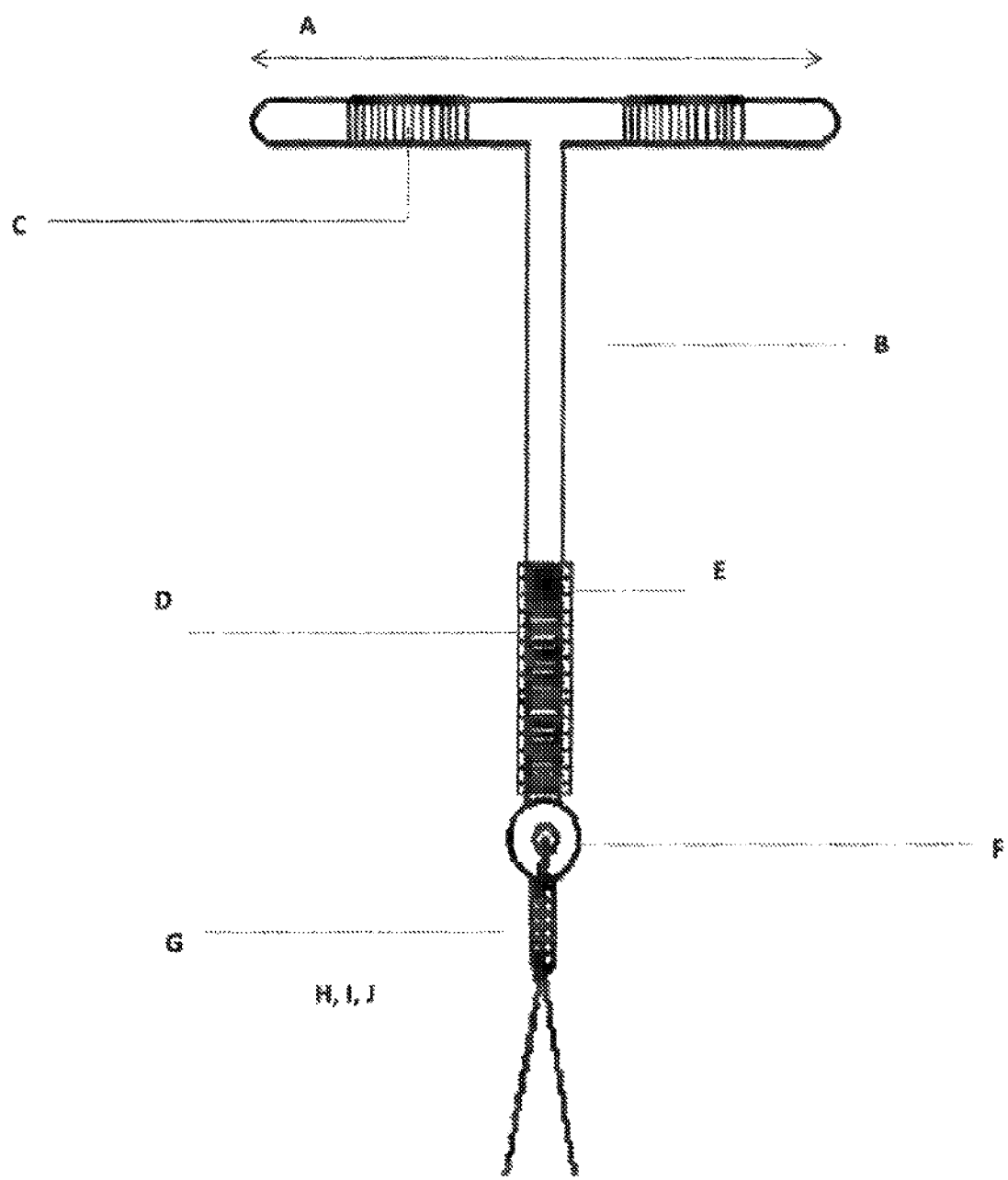
FIG. 1 Frontal View of a plastic T-shaped frame which is 1.7 mm in diameter and has the following measurements: Horizontal arm 18.0±2 mm-32.0±2 mm in length (A): the vertical post measures 26.0±2 mm-36.0±2 mm (B) and at its lower end it has a plastic or copper sphere with a diameter of 3.1 mm (F). Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.
Figure 2:
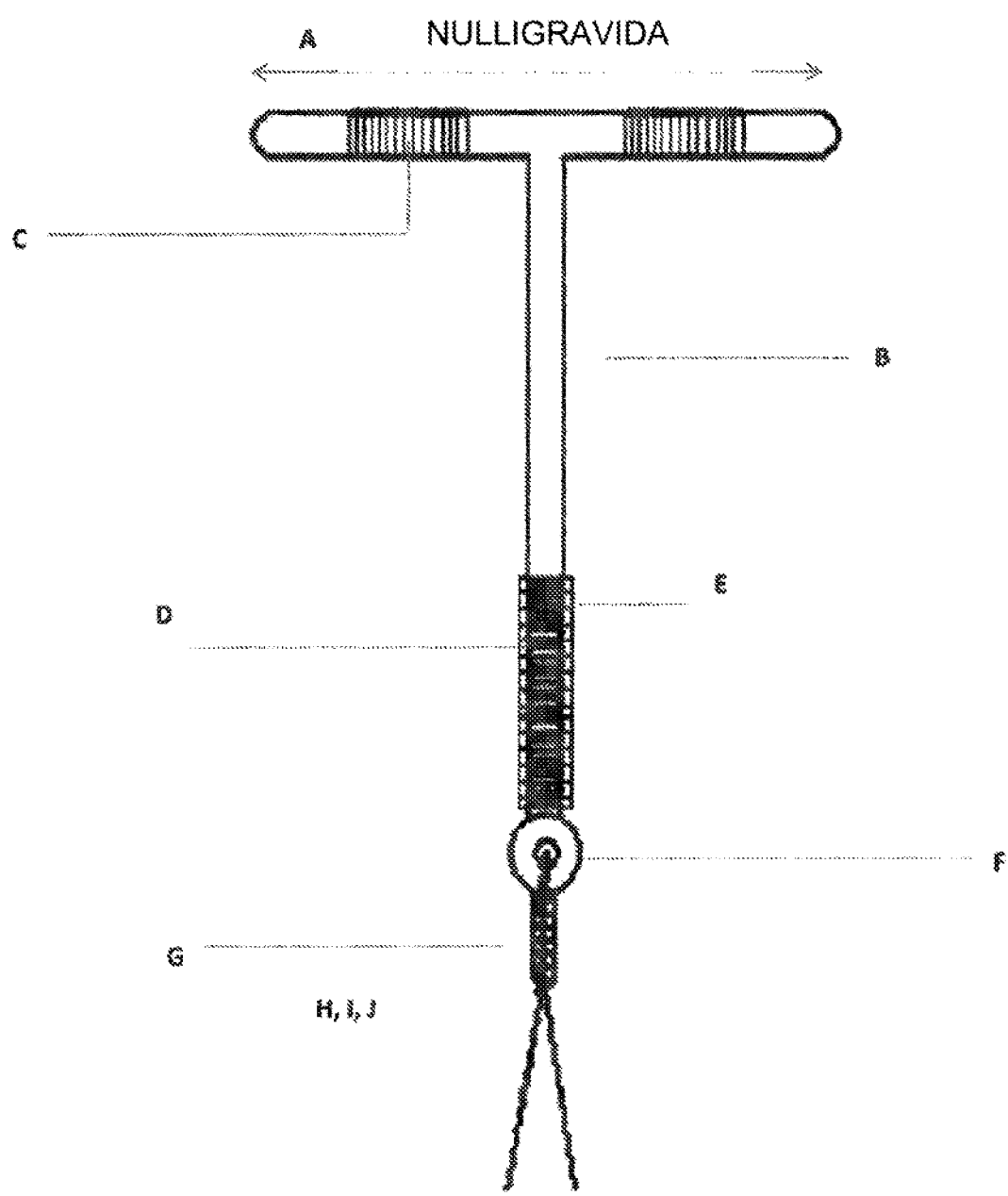

Nulligravida FIG. 2 Frontal View of a plastic T-shaped frame which is 1.7 mm in diameter and has the following measurements: Horizontal arm 18.0±2 mm in length (A): the vertical post measures 26.0±2 mm (B) and at its lower end it has a plastic or copper sphere with a diameter of 3.1 mm (F). Wound on each side of the horizontal arm is a strand of copper measuring 0.25 mm to 0.26 mm in diameter and 36.0±2 mm$^2$ each, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

Figure 3:
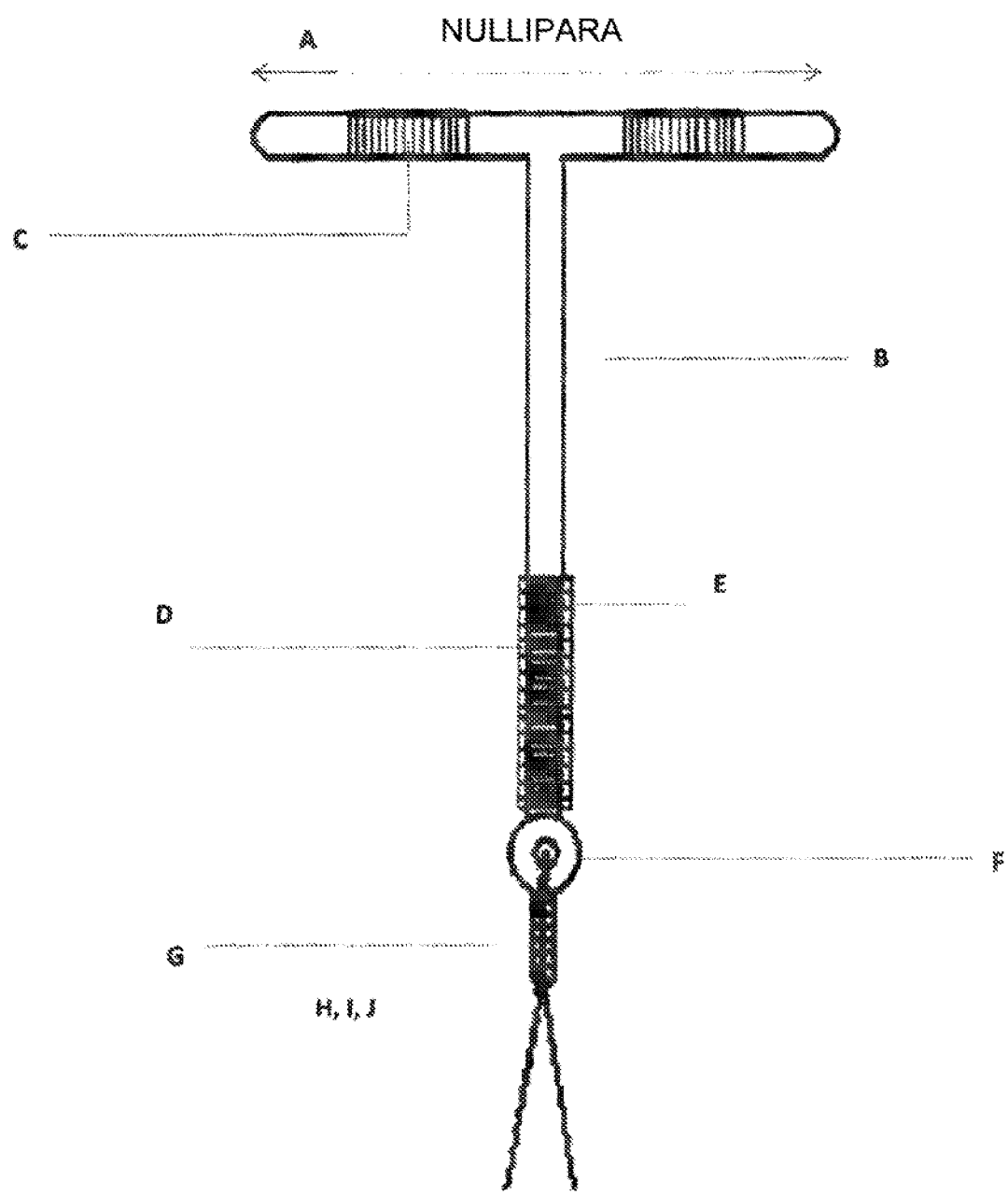

Nullipara: FIG. 3.

Frontal View of a plastic T-shaped frame which is 1.7 mm in diameter and has the following measurements: Horizontal arm 22.0±2 mm in length (A): the vertical post measures 28.0±2 mm (B) and at its lower end it has a plastic or copper sphere with a diameter of 3.1 mm (F).

Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

Figure 4:
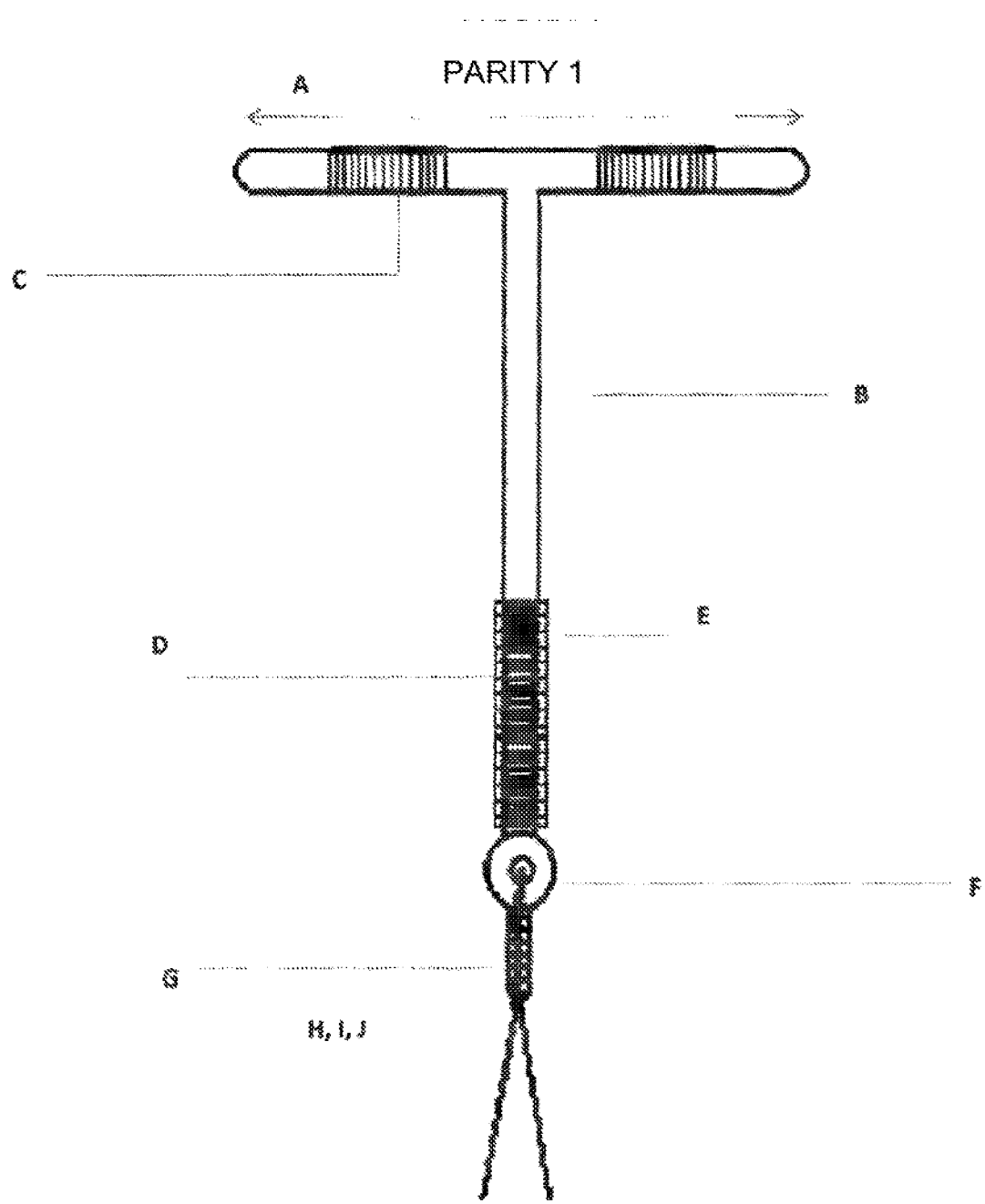

Parity 1 FIG. 4

Frontal View of a plastic T-shaped frame which is 1.7 mm in diameter and has the following measurements: Horizontal arm 24.0±2 mm in length (A): the vertical post measures 30.0±2 mm (B) and at its lower end it has a plastic or copper sphere with a diameter of 3.1 mm (F). Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

Figure 5:
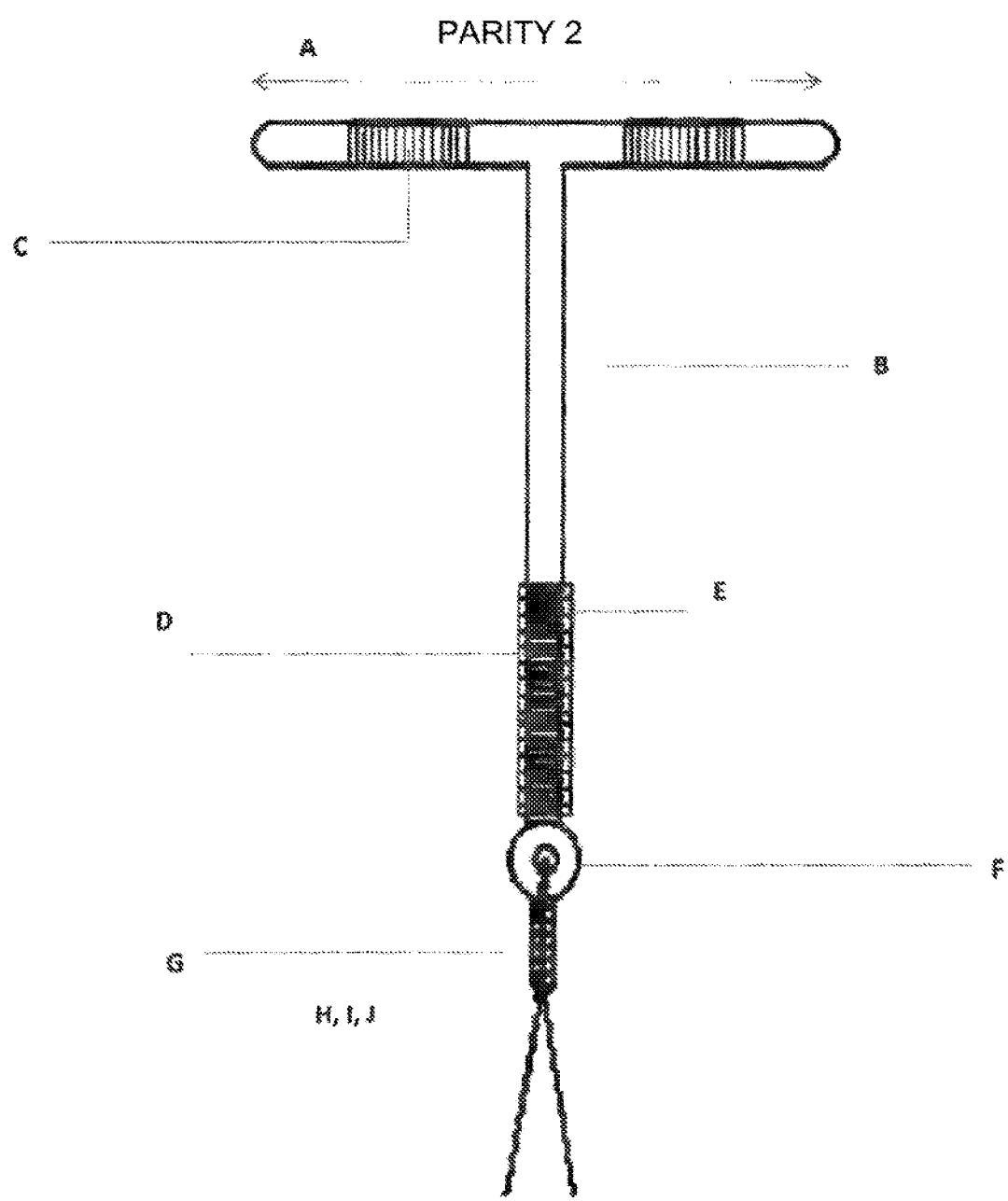

Parity 2 FIG. 5

Frontal View of a plastic T-shaped frame which is 1.7 mm in diameter and has the following measurements: Horizontal arm 26.0±2 mm in length (A): the vertical post measures 32.0±2 mm (B) and at its lower end it has a plastic or copper sphere with a diameter of 3.1 mm (F). Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

Figure 6:
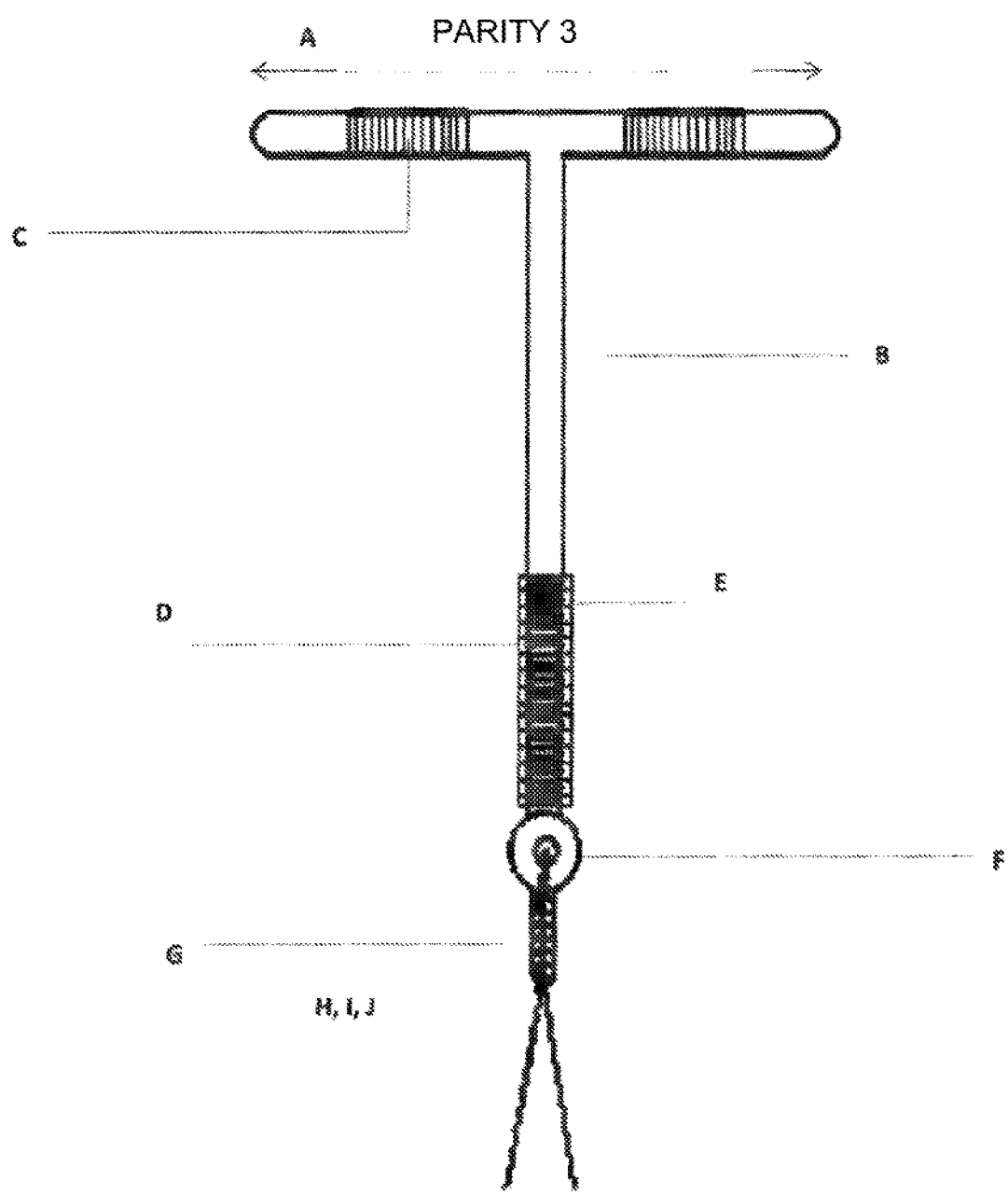

Parity 3 FIG. 6

Frontal View of a plastic T-shaped frame which is 1.7 mm in diameter and has the following measurements: Horizontal arm 28.0±2 mm in length (A): the vertical post measures 34.0±2 mm (B) and at its lower end it has a plastic or copper sphere with a diameter of 3.1 mm (F). Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E). Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

Figure 7:
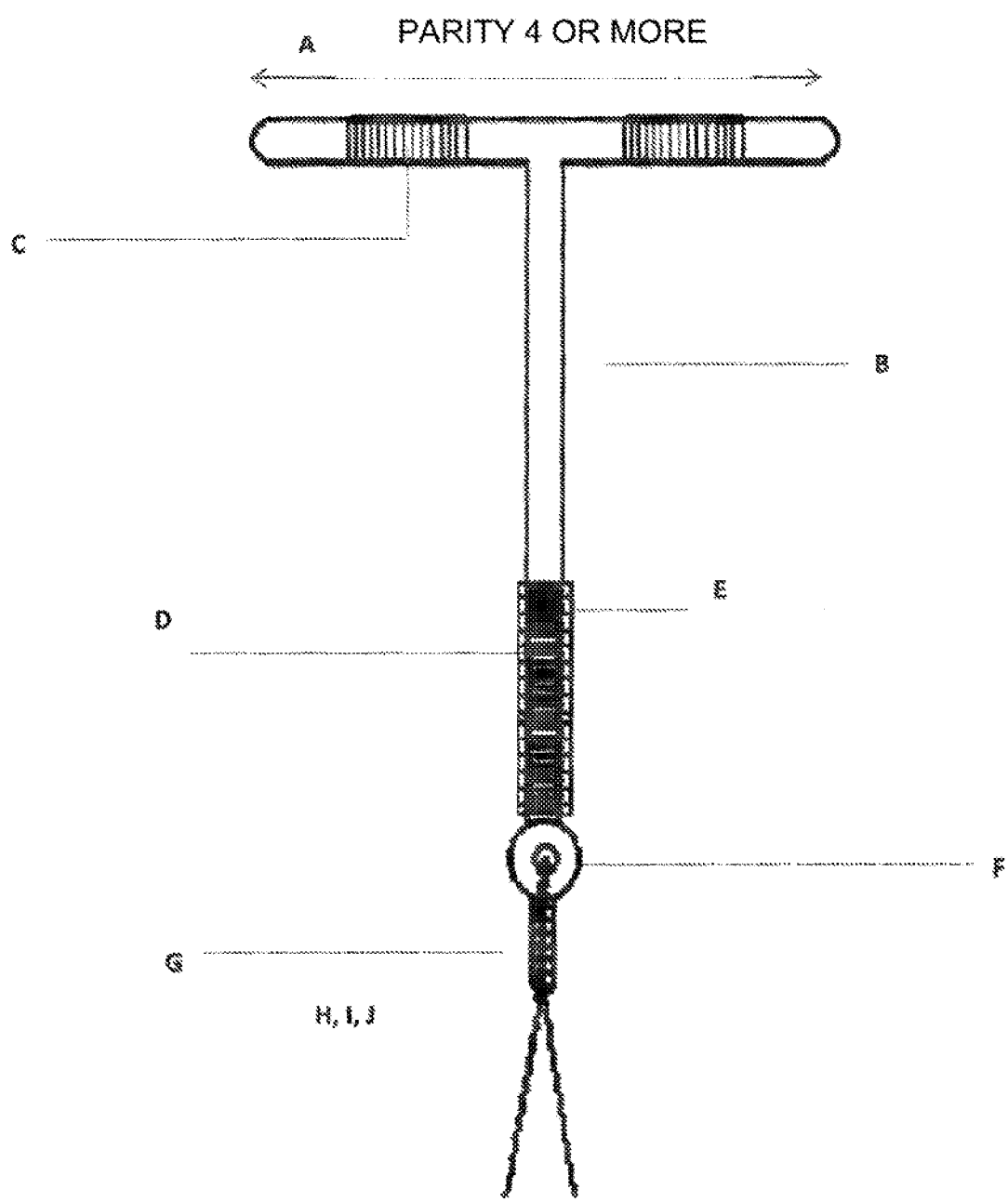
Figure 8:
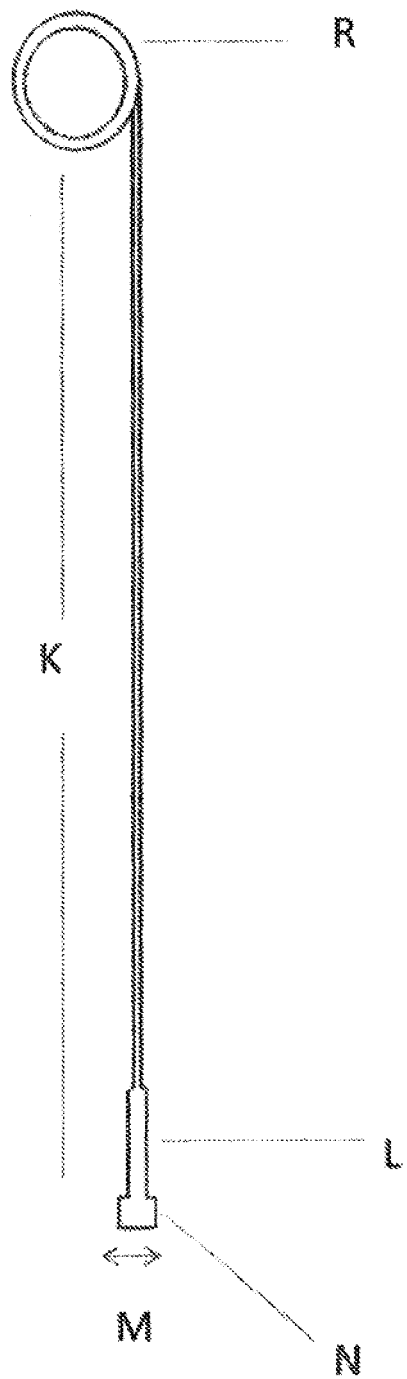

Parity 4 or more FIG. 7 Frontal View of a plastic T-shaped frame which is 1.7 mm in diameter and has the following measurements: Horizontal arm 32.0±2 mm in length (A): the vertical post measures 36.0±2 mm (B) and at its lower end it has a plastic or copper sphere with a diameter of 3.1 mm (F). Wound on each side of the horizontal arm is a strand of copper each measuring 0.25 mm to 0.26 mm in diameter and 36.0±2 mm$^2$, totaling 72.0±2 mm$^2$ (C). At the bottom of the vertical post are wound two superimposed filament layers of copper each with 100 mm$^2$ of copper with a total of 200 mm$^2$ (D) and whose coils are spaced at 0.30 mm (E).

Inside the sphere are placed the ends of a length of coiled copper wire or Solomon Bar, Celtic Knot or Bracelet with 146 mm$^2$ to 250 mm$^2$ (G) totaling a 418-mm$^2$ area of copper.

FIG. 8 Plunger

Front view of a plastic, piston-shaped device with a length (K) of 188-193 mm, on one of its ends in cylindrical space (L) with a length of 10 mm, lower diameter (M) 2.5 mm, outer diameter (N) 3.3 mm and the other end is shaped like a handle or grip (R).

BIBLIOGRAPHICAL REFERENCES

1. Zur Hausen H, 1996: Papillomavirus infections—A major cause of human cancers. Biochim. Biophys Acta 1288: 55-78
2. Virus delPapiloman Humano Dr. José de Jésus Curiel Newscure
3. Cuentas en Salud Reproductiva y Equidad de Genero Primera Edición 2011 Instituto Nacional de Salud Pública
4. Intrauterine device use, cervical infection with human papillomavirus, and risk of cervical cancer: a pooled analysis of 26 epidemiological studies. Xavier Castellsague, Mireña Diaz, Salvatore Vaccarelia, Silvia de Sanjose. Nubia Muñoz, Rolando Herrero, Silvia Franceschi. Chris M Meijer. Et al. Intrauterine device use, cervical infection with human papillomavirus, and risk of cervical cancer a pooled analysis of 26 epidemiological studies Lancet Oncol. 2011 Oct. 12; (11):1023-1031.
5. REREGISTRATION ELIGIBILITY DECISION FOR COPPERS Case Nos. 0636, 0649, 4025, 4026 Debra Edwards, Ph.D. Director, Special Review and Reregistration Division EPA
6. Cu Copper Development Association International Copper Association Mexico Copper Alliance
7. El Cáncer Cervicouterino, su Impacto en México y el por qué no funciona el programa nacional de Detección Oportuna. Ana C. Hidalgo Martínez Centro de Investigación sobre enfermedades Infecciosas Instituto Nacional de Salud Pública. RevBiomed 2006 17; 81-84
8. ABORTO CLANDESTINO The Alan Guttmacher Institute N. Rutenber, M. Ayad. L. H. Ochoa and M. Wilkinson, "Knowledge and Use of Contraception", DHS Comparative Studies, No. 6, Julio de 1991, Cuadro 4.1; And special analyses of Demographic and Health Surveys by the AGI
9. Reynoso L, Zamora G, Giner J, Gonzalez M., y Aznar R., Medidas de la Cavidad uterina en mujeres mexicanas, Ginec. Obstet, Mex. J. Vol 45 Year XXXIV, No. 271, May 1979.
10. Reynoso L, Zamora G., Gonzalez, Diddi M., Lozano M., Aznar R., «Uterine metrology in «Mexican women», in «Biomedial Aspects of IUDs», pp 119-124, published in the UK and Europe by Mtp. Press, Lancaster England RG 137 ISBN 085200, 1982

REFERENCES

Descriptive Notes

1. Coils: synonym helix: helicoidal; curve: curved, arched; bent; convex; concave.
2. ContracepFertil Sex. 1998 November; 26 (11):781-9. [Atomic absorption spectrophotometry study of copper ion released by copper-bearing intrauterine devices]. Berthou J1, Chretien F C, Driguez P A. Author information
3. Los iones y la Salud El Ediciones by 2002 Argentina.
4. Manual de nudosmarinos. http://www.marina.mil.pa.static.fHes
5. Invasive Cervical Cancer and Intrauterine Device USE International Journal of Epidemiology ©International Epidemiological Association 1991 DEBORAH L LASSISE***. DAVID A SAVITZ'f. RICHARD F HAMMAN*. ANNA E BARON*, LOUISE A BRINTONt AND ROBERTS LEVINES
6. REREGISTRATION ELIGIBILITY DECISION FOR COPPERS Case Nos. 0636, 0649, 4025, 4026 Debra Edwards, Ph.D. Director, Special Review and Reregistration Division EPA
7. Cu Copper Development Association International Copper Association Mexico Copper Alliance
8. Intrauterine device use, cervical infection with human papillomavirus, and risk of cervical cancer: a pooled analysis of 26 epidemiological studies. Xavier Castellsague, Mirena Diaz, Salvatore Vaccarelia, Silvia de Sanjose. Nubia Munoz, Rolando Herrero, Silvia Franceschi. Chris M Meijer. Et al. Intrauterine device use, cervical infection with human papillomavirus, and risk of cervical cancer a pooled analysis of 26 epidemiological studies Lancet Oncol. 2011 Oct. 12; (11):1023-1031.
9. Cuentas en Salud Reproductiva y Equidad de Genero Estimación 2009, Comparativo 2003-2009 Gobierno Federal. Instituto Nacional de Salud Pública Mexico 2011

Explanatory Annex

1. Radiopacante. Medio de contraste positivo más utilizado sulfato de bario y compuestos yodados: Ba S04 Medios de contraste en imagenologia Agustina Chavez Sanchez May 17, 2013
2. Coils: synonym helix: helicoidal; curve: curved, arched; bent; convex; concave.
3. Contracept. Fertil Sex. 1998 November; 26 (11): 781-9 [Atomic absorption spectrophotometry study of copper ion release by copper-bearing intrauterine devices]. Berthou J1, Chretien F C, Driguez P A. Author information
4. Los iones y la Salud El Ediciones by 2002 Argentina.
5. Manual de nudosmarinos. www.marina.mil.pa.static.files Having described the invention fully as above, the contents of the following claims are claimed as property:

1. A uterine cervical device comprising:
a T-shaped frame formed of inert plastic material having between 15 and 23 weight percent radiopaque material, the radiopaque material being a combination of barium sulfate and titanium oxide, said T-shaped frame having a horizontal arm having a length of between 17.8 millimeters and 32.2 millimeters, said T-shaped frame having a vertical post extending from the horizontal arm, the vertical post having a length of between 25.8 millimeters and 36.2 millimeters and a diameter of 1.7 millimeters, the horizontal arm having portions on opposite sides of the vertical post;
a sphere affixed to the vertical post, said sphere being formed of inert plastic or copper, said sphere having a diameter of 3.1 millimeters;
a strand of copper wound on each of the portions of the horizontal arm, said strand of copper having a diameter of between 0.25 and 0.26 millimeters and having a total area of copper of between 35.8 and 36.2 square millimeters;
a pair of copper filaments wound on the vertical post, each of said pair of copper filaments having a diameter of 0.25 and 0.26 millimeters and a total area of copper of 100 square millimeters, the pair of copper filaments extending for a distance of between 20 and 25 millimeters;
a length of a copper filament having an area of between 146 and 250 square millimeters wound in a shape of a Soloman bar or a Celtic knot or a bracelet, wherein said length of the copper filament being positioned distal said sphere on said T-shaped frame, said sphere positioned between the vertical post and said length of the copper filament; and a low-density polyethylene thread having a length of 20 centimeters and a diameter of between 0.20 and 0.30 millimeters, said low-density polyethylene thread being affixed to said T-shaped frame and positioned inside said length of copper filament, a total amount of copper of said strand of copper and said pair of copper filaments and said length of copper filaments being between 418 and 524 square millimeters.

2. The uterine cervical device of claim 1, wherein the horizontal arm has a length of between 17.8 and 18.0 millimeters, wherein the vertical post has a length of between 25.8 and 26.2 millimeters.

3. The uterine cervical device of claim 1, wherein the horizontal arm has a length of 21.8 and 22.2 millimeters, wherein the vertical post has a length of between 27.8 and 28.2 millimeters.

4. The uterine cervical device of claim 1, wherein the horizontal arm has a length of between 23.8 and 24.2 millimeters, wherein the vertical post has length of between 29.8 and 30.2 millimeters.

5. The uterine cervical device of claim 4, wherein the horizontal arm has a length of between 25.8 and 26.2 millimeters, wherein the vertical post has length of between 31.8 and 32.2 millimeters.

6. The uterine cervical device of claim 4, wherein the horizontal arm has a length of between 27.8 and 28.2 millimeters, wherein the vertical post has length of between 33.8 and 34.2 millimeters.

7. The uterine cervical device of claim 4, wherein the horizontal arm has a length of between 31.8 and 32.2 millimeters, wherein the vertical post has length of between 35.8 and 36.2 millimeters.

8. The uterine cervical device of claim 1, further comprising:

a plunger having a length of between 188 and 193 millimeters, said plunger having a plastic frame having a cylindrical end, the cylindrical end defining a recess with a length of 2 centimeters and an inner diameter of 2.5 millimeters and an outer diameter of 3.3 millimeters, the cylindrical end receiving the uterine cervical device therein.

9. The uterine cervical device of claim 1, the inert plastic selected from the group consisting of low-density polyethylene, polypropylene, polyester and silicone elastomer.

10. A method of preventing uterine cervical cancer caused by a human papillomavirus, the method comprising:

placing the uterine cervical device of claim 1 inside a uterine cavity of a patient.

* * * * *